United States Patent [19]
Huo et al.

[11] Patent Number: 6,030,416
[45] Date of Patent: Feb. 29, 2000

[54] MEDICAL IMPLANTS OF STRETCH-CRYSTALLIZABLE ELASTOMERS AND METHODS OF IMPLANTATION

[75] Inventors: Peter P. Huo; Stephen Q. Zhou, both of Irvine; Christine J. Y. Liau, La Palma, all of Calif.

[73] Assignee: Pharmacia & Upjohn AB, Stockholm, Sweden

[21] Appl. No.: 09/023,391

[22] Filed: Feb. 13, 1998

[51] Int. Cl.[7] ................................. A61F 2/16; A61F 2/02
[52] U.S. Cl. ................................................ 623/6; 623/11
[58] Field of Search ........................................ 623/4, 6, 11

[56] References Cited

U.S. PATENT DOCUMENTS

| | | | |
|---|---|---|---|
| 4,573,998 | 3/1986 | Mazzocco | 623/6 |
| 4,702,244 | 10/1987 | Mazzocco | 623/6 X |
| 4,946,470 | 8/1990 | Sulc et al. | 623/6 |
| 5,492,993 | 2/1996 | Saam et al. | |
| 5,702,441 | 12/1997 | Zhou | 623/6 |

*Primary Examiner*—Jeffrey A. Smith
*Attorney, Agent, or Firm*—Oppenheimer, Wolff & Donnelly

[57] ABSTRACT

Reduced trauma medical implants and methods for their use are disclosed wherein at least a portion of the implant is formed of a stretch-crystallizable elastomeric material formulated to exhibit the property of stretch crystallization upon substantial elongation of the implant to form stable, small-incision implant configurations having at least one dimension substantially reduced for insertion through a surgical incision that is small relative to the incision size necessary to implant the unstretched implant. Exemplary embodiments include intraocular implants formed of optically clear, high refractive index stretch-crystallizable silicone elastomers formulated to stretch crystallize at near ambient temperatures upon elongations greater than or equal to 300% and to recover their original configuration immediately upon exposure to body temperature following implantation.

24 Claims, 4 Drawing Sheets

MEDICAL IMPLANTS OF STRETCH-CRYSTALLIZABLE ELASTOMERS AND METHODS OF IMPLANTATION

FIELD OF THE INVENTION

The present invention relates in general to stretch-crystallizable elastomeric medical implants and to methods for the insertion and placement of such medical implants, particularly optical lenses. More particularly, the present invention is directed to elastomeric, highly extensible implants formed from stretch-crystallizable elastomers, preferably silicone, which are significantly stretched to induce stable, yet reversible, higher melting point crystals to produce stable, elongated, small cross-section deformed implant configurations for use in small-incision implantation techniques. Within seconds of being inserted into the body and subjected to normal body temperature the stretch induced crystals melt allowing the implants to return to their original dimensions, shapes, and physical characteristics.

BACKGROUND OF THE INVENTION

There are many well-developed applications and techniques known in the art for the replacement or augmentation of natural body parts with medical implants. These medical implants can be divided into two general classes of implanted medical devices. The first class includes implants which perform useful and essential functions based upon a variety of mechanical properties, including strength and flexibility. Examples of such implants include replacement heart valves and artificial joints. The second class includes implants which perform useful and essential functions by virtue of the physical shape of the implant rather than its structural or mechanical properties. Examples of this class of implants include cosmetic devices designed to augment or replace missing tissue or, more importantly, artificial optical lenses designed to augment or replace the natural lens of the eye.

Although medical implants of this second class have been successfully used for many years, their use is not without problems. One of the primary difficulties is the physical trauma caused by the surgical incisions that must be made in the body to position the implants. It is well known in the medical art that reducing the size of the surgical incision needed for the implantation procedure will reduce this trauma. At present, reducing the size of the surgical incision is best achieved, where possible, by reducing the size of the implant itself. Alternatively, recent research and development has focused on reducing the size of the surgical incision itself. Through the utilization of arthroscopic or microsurgery techniques and instruments, implanting surgeons can confine the physical impact of the surgical procedure to the desired target location through small, often remote incisions. These small incisions reduce much of the trauma normally associated with surgery using conventional large-incision techniques. As a result, much of the discomfort, healing time and complications that may occur can be reduced with small-incision techniques.

This research has not been easy because the volume, dimensions, and relative rigidity of the conventional implants place practical limits on the available reduction of incision size. Though relevant to many types of prosthetic and cosmetic implants, this problem is typified by artificial optical lenses, known as intraocular lenses or "IOLs". These artificial lenses, are implanted into the eye to replace or augment the natural lens and it ability to focus light onto the retina of the eye. In this functional context, it is the shape and volume of the lens, in conjunction with the refractive index of the lens material, that causes the light entering the eye and passing through the lens to be focused properly onto the retina permitting clear vision.

Presently, most practical intraocular lens implantation procedures require an incision in the eye that is greater than 3 millimeter (mm) to 4 mm. In most cases, an intraocular lens is implanted after the removal of the damaged or cataractous natural lens. Currently, the procedure for the removal of the natural lens requires an incision of at least 3 mm to 4 mm. However, the typical intraocular lens implant includes an optical light focusing lens portion and minor projecting structural features ("haptics") which assist with the placement and retention of the lens within the eye following implantation. Most currently available IOLs have a minimum diameter on the order of 6 mm and a minimum thickness of 1 mm to 2 mm. More recently, lenses known as "full-size optics", intended to completely replace the natural lens, have been developed having minimum diameters ranging from 8 mm to 13 mm and minimum thicknesses ranging from 3 mm to 5 mm. Thus, a surgical incision that is at least as large as the minimum dimension of the optical implant must be made. There are significant drawbacks to the use of any incision in the eye, especially ones that are greater than 3 mm to 4 mm. These drawbacks include post-operative astigmatism or corneal distortions, as well as the potential for increased complications and healing time.

One method known for reducing the size of the surgical incision associated with implanting an intraocular lens is to form the lens from a relatively flexible material which is folded or rolled to reduce the size of one dimension prior to inserting the lens into the eye. Once implanted, the lens is intended to unfold and return to its original shape. Foldable lenses, although adequate for their intended purposes, have drawbacks which limit their use for small-incision surgical implantation and may make them impractical. For example, when folded, only one of the three dimensions, the diameter or the width, can be reduced, and then, by only half. At the same time, one of the other dimensions, the thickness, is necessarily doubled while the third dimension remains unchanged. The minimum incision size is thus limited to one half of the largest dimension, which in the case of currently available lens configurations, remains on the order to 4 mm to 6 mm in length. Further compounding matters, folding the lens may produce permanent creases or deformation in the optical portion of the lens, causing visual distortion following implantation.

An alternative method that has been proposed for reducing incision size during implantation is the use of expansile lenses made of materials such as hydrogels. The hydrogel lens is desiccated prior to insertion to reduce the overall volume and dimensional characteristics of the lens. Following implantation, the hydrogel material is intended to rehydrate and expand back to its original size. While such hydrogel lenses are capable of significant reductions in size, the current state of the hydrogel art requires a re-hydration period following implantation ranging from 3 hours to 24 hours. This length of time is impractical because the implanting surgeon is unable to determine whether the lens is properly positioned in the eye prior to complete hydration. As a result, implanting surgeons may be reluctant to use such lenses because they require waiting prior to close the implantation incision until the surgeons are certain that access to the interior of the eye is no longer necessary to reposition the lens.

Other methods for the small-incision surgical implantation of intraocular lenses have been proposed with little success. In one proposal, a transparent balloon lens in its empty or deflated state is to be inserted into the eye through a small incision. Once inserted into the eye, the proposed balloon lens is to be filled with a highly refractive material to inflate the lens to its final configuration. To date, balloon lenses have proven to be impractical as they are difficult to manufacture and inflate with any degree of accuracy or control following implantation. Further, there are unsolved difficulties with materials, the removal of bubbles, and with the sealing of the lenses.

Similarly, injectable lenses have been proposed to replace the natural lens in situ wherein a liquid polymer would be injected into the naturally occurring lens capsule and allowed to cure into its final configuration. Present technology has been unable to produce such lenses because it is difficult to produce predictable optical power and resolution with biocompatible materials.

A more practical and realizable method for reducing the size of the surgical incision used when implanting an intraocular lens is disclosed in currently pending U.S. patent application Ser. No. 08/607,417, Now U.S. Pat. No. 5,702,441. With this technique, lenses are formed from a memory material, i.e., a material having the ability to be shape transformable, such as elastomeric or gelatinous materials capable of substantial recoverable deformation in all directions. These lenses are implanted through a small incision in the eye using a small-diameter, tubular ejector. Following implantation, the gelatinous lens implants immediately reassume their pre-implant shapes and configurations, allowing the implanting surgeon to confirm proper placement and completion of the implantation procedure.

However, even this technology can be improved upon. For example, when such lenses are deformed and placed within the tubular ejector, the lenses are forced into a shape having a high surface-area-to-volume ratio. Under these conditions, there may be strong elastomeric forces exerted by the deformed lens on the tubular ejector as the deformed lens tries to recover its original size and shape. These forces, coupled with the large surface-area-to-volume ratio, may cause the deformed lens to be difficult to push out of the tubular ejector and into the eye.

Accordingly, one of the objectives of the present invention is to provide implantation methodology that will allow the rapid and easy insertion and positioning of medical implants through very small surgical incisions relative to the size of the implant without the use of complicated or sophisticated techniques or implant delivery systems.

It is an additional object of the present invention to provide surgical implants such as intraocular lenses that can be inserted and positioned within a patient through a very small incision relative to the shape, size, and volume of the implant.

It is yet another object of the present invention to provide stretch-crystallizable silicone intraocular lenses that are optically clear, have high refractive indices, and that can be stretched into long, thin rods or blades which crystallize and stabilize at temperatures below normal body temperature, and which reassume their pre-stretch-crystallized shape, contours and physical characteristics within seconds after being implanted into the eye.

SUMMARY OF THE INVENTION

These and other objects are achieved by the compositions, implants, methods, and associated apparatus of the present invention which can rapidly and simply insert and position stretch-crystallizable deformable medical implants into a patient's body. In accordance with broad, functional aspects of the present invention, the medical implants of the present invention are formed from novel, biocompatible stretch-crystallizable elastomers, preferably silicone, with refined physical properties which, as they are stretched significantly, on the order of 300% or greater, form higher melting-point molecular crystals due to the new orientation of their stretched molecular structures. As a result, they are capable of stretching and deforming into stabilizible, easily manipulated, long, thin rods or blades at temperatures below normal body temperature, but temperatures which are not so low as to be expensive or difficult to reach or to work with. Once implanted, the stretched, higher melting point crystals warm and melt causing the implants to recover their original sizes, shapes, contours, and properties immediately after being exposed to higher body temperatures.

In accordance with the teachings of the present invention the novel stretch-crystallizable elastomers are formulated to have practical crystal melting temperatures that allow implants formed of the elastomers to be stretch crystallized at near ambient temperatures into stable small-incision configurations in very short, convenient time periods with minimal effort. If desired, cooling the stretched implants will accelerate the formation of the internal, stretch induced micro-crystals which ftnction as transient cross-linker-like "fillers" to molecularly bind the deformed implants into stable, yet reversible, shape-frozen configurations. These crystallized, shape-frozen configurations can be maintained easily with simple cooling which allows the implanting surgeon to manipulate and position the implants without special tools or cooling devices or fear that the implants will prematurely "melt" back to their original configurations. Medical implants formed from these stretch-crystallizable materials solve the problem of providing practical apparatus and methods for the implantation of medical devices that significantly reduce the size of surgical incisions needed to implant the devices.

In accordance with the teachings of the present invention, materials that exhibit stretch crystallization are beneficial in any application in which it is desired to implant an elastomeric medical apparatus through a passage smaller than the implant's original dimensions. One of the primary benefits in using the stretch-crystallizable materials of the present invention is that the materials can be stretched and crystallized at temperatures lower than body temperature (approximately 37° C.). Further, the medical implants formed in accordance with the teachings of the present invention can be implanted through very small surgical openings directly or with the use of small-diameter, generally tubular placement devices to provide reduced trauma access to target sites within a patient's body.

The novel compositions and associated implants and methods of the present invention have numerous characteristics and advantages that distinguish them from the prior art. For example, the stretch-crystallizable elastomeric materials are biocompatible and, for optical purposes are formulated to be optically clear with relatively high refractive indices analogous to those of the natural human lens. Moreover, the elastomers are "tuned" by specific formulation to exhibit stretch crystallization at temperatures in usable ranges relative to ambient or room temperature (approximately 20° C.) and body temperature (approximately 37° C.). What is more, the elastomers are capable of significant elongation wherein they develop increased tensile strength due to the formation of higher melting-point micro-sized crystals during stretching which act as transient reinforcing fillers. Yet they exhibit 100% post-stretch recovery to their original configurations because they lack conventional, non-stretchable strengthening fillers such as the fumed silica cross-linkers found in prior art elastomers. Importantly, melting recovery to original implant configurations occurs at body temperature. Thus, the materials of the present invention can be formulated to provide stretch-crystallization temperatures ranging from −100° C. to 50° C. and recovery temperatures ranging from 25° C. to 50° C.

These materials produce unprecedented implants intended for small-incision surgical implantation. For example, the implants of the present invention are capable of being stretched in at least one direction to a dimension that is on the order of 300% to 600% its original size. Thus, while the volume of the implants remains constant, their three-dimensional shapes can be significantly altered into stable, very small-dimensioned forms that will readily and easily pass through very small incisions or small-bore implantation devices with minimal effort. When implanted through an implantation apparatus, the stretch-crystallized implants do not exert significant elastomeric force against the internal walls of the device. Thus, only a small force is needed to push the crystallized material implant into, through, and out the device into the target implantation site. The stretch-crystallized implants of the present invention also exhibit recoverable deformation within seconds after being implanted and exposed to normal body temperatures. This provides the implanting surgeon with immediate confirmation of a successful implantation without the need for complex, post-implantation manipulation or techniques.

The present invention is particularly well suited for the production and implantation of optical lenses and implantable contact lenses into the eye for corrective purposes or for replacement (pseudophakic) purposes. The exemplary optical lens implants of the present invention are formed from biocompatible stretch-crystallizable silicone elastomers. Exemplary silicone elastomers are formed in accordance with the teachings of the present invention by the polymerization of what is known in the art as an $F_3$ monomer, such as methyl(3,3,3-triflouropropyl)siloxane, in an exemplary cis/trans ratio ranging from approximately 40/60 to 100/0, into a homopolymer or a copolymer with a monomer having a higher refractive index than the $F_3$ monomer, such as, what is known in the art as a $D_3(2Ph)$ monomer like hexaphenylcyclotrisiloxane. The resulting exemplary polymer has a composition of from 60% to 100% of the $F_3$ monomer and from 0% to 40% of the $D_3$ monomer. These exemplary stretch-crystallizable elastomers are biocompatible, optically transparent and exhibit a refractive index on the order of 1.4 making them particularly well suited for constructing IOLs. The optical lens implants may be configured as full-sized lenses, having diameters on the order of 8 mm to 13 mm and center thicknesses from 3 mm to 5 mm, which can completely fill the capsular bag, or as conventionally sized, single or multipiece 5-mm to 7-mm optics with 1-mm to 2-mm center thicknesses and which may include one or more radially extending haptic support structures. The cross-sectional shape of the optic lens may be any shape, including plano-convex, biconvex, converging meniscus, diverging meniscus, plano-concave, biconcave, and balloon shaped.

Broadly speaking, one embodiment of the associated implantation method of the present invention simply involves stretch crystallizing the elastomeric implant at a temperature lower than normal body temperature and directly inserting the deformed implant into a target site within a patient's body. For example, after being crystallized to form a long, thin relatively rigid rod, the implant may be manipulated by the surgeon with forceps, or other similar apparatus, and inserted directly into the body through a relatively small surgical incision. Once inside the body, the implant is exposed to normal body temperature, and, within seconds, the implant returns to its pre-stretch-crystallized size and configuration.

In an alternative embodiment, the stretch-crystallized implant may be loaded into an implantation device having a small-diameter, generally tubular outlet. The device is inserted and positioned into a target site within the patient's body and the implant is pushed through the tubular outlet into the target site. If desired, the diameter of the elongate tubular outlet can be sufficiently small to enable the outlet to function as a puncturing cannula analogous to a hypodermic needle capable of forming its own access pathway. Alternatively, a small surgical incision can be made utilizing conventional surgical incision techniques, and the tubular outlet can be inserted therethrough.

In either embodiment, the present invention allows an intraocular lens implant to be implanted into the eye through a very small surgical incision that may range from 1 mm to 4.5 mm.

Other objects, features, and advantages of the present invention will become apparent to those skilled in the art from a consideration of the following detailed description taken in conjunction with the accompanying drawings which illustrate, by way of example, the principles of the present invention in the context of an exemplary IOL implant, but which are equally relevant to other implants which can include elastomeric portions.

DETAILED DESCRIPTION OF THE EXEMPLARY EMBODIMENTS

Figure 1:
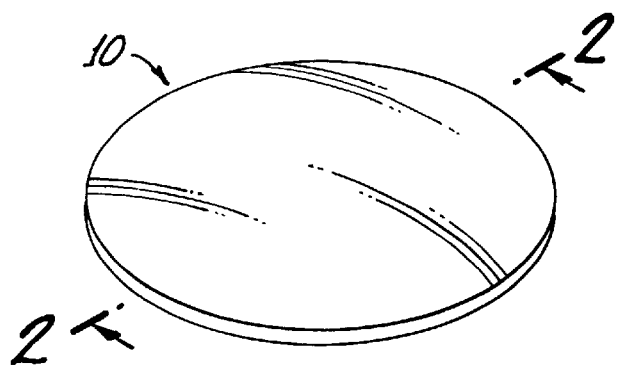
FIG. 1 is a perspective view of an exemplary stretch-crystallizable implant configured as an intraocular lens implant in accordance with the present invention, particularly illustrating an unstretched configuration of the implant.
Figure 2:
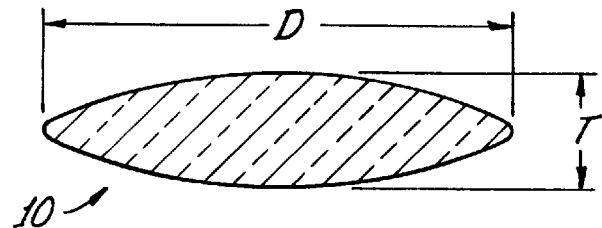
FIG. 2 is a cross-sectional view of the unstretched exemplary implant taken along line 2—2 of FIG. 1.

Referring more particularly to the drawings, an exemplary stretch-crystallizable and shape-transformable medical implant 10 produced in accordance with the teachings of the present invention is illustrated in FIGS. 1 and 2. For purposes of explanation and without limiting the scope of the present invention, exemplary implant 10 is illustrated as an intraocular lens to demonstrate the unique features of the present invention in a simple context. Alternative function implants are contemplated as being within the scope of the present invention as will be understood by those skilled in the art. Those skilled in the art will also appreciate that exemplary lens implants must be optically transparent and possess an appropriate refractive index to function as a lens. However, these additional properties are not essential to all implants produced in accordance with the teachings of the present invention.

Figure 3:
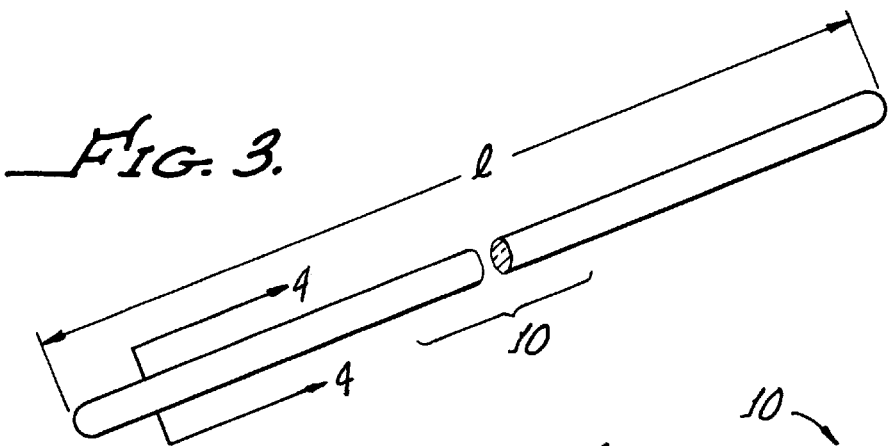
FIG. 3 is a perspective view of the exemplary stretch-crystallizable implant of the present invention, particularly illustrating a stretched configuration of the implant.
Figure 4A:
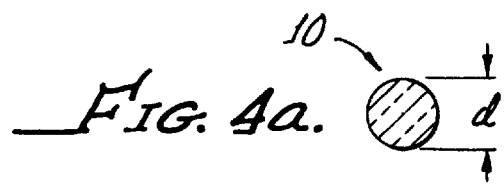
FIG. 4A is a cross-sectional view of the stretched exemplary implant taken along line 4—4 of FIG. 3.
Figure 4B:
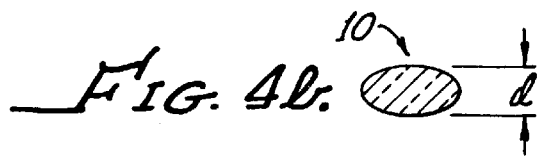
FIG. 4B is a alternative cross-sectional view of the stretched exemplary implant taken along line 4—4 of FIG. 3.

Exemplary implant 10 is formed from a stretch-crystallizable elastomer such as one of the exemplary silicone compositions discussed herein. When stretched significantly, these novel elastomers form molecular or "micro-sized" crystals with relatively higher melting points than those of their unstretched states due to the now aligned molecular orientation of the stretched elastomeric structures. FIGS. 1 and 2 illustrate exemplary implant 10 in an unstretched configuration, and FIGS. 3, 4A, and 4B illustrate the implant in a stretched and stable shape-frozen configuration which facilitates its uncomplicated implantation through a small incision. Those skilled in the art will appreciate that a significant degree of stretching is necessary to induce stretch crystallization. This is completely unlike the simple, localized deformation utilized with foldable implants.

Because of the uniquely designed and fine-tuned physical properties of the stretch-crystallizable elastomers of the present invention, exemplary implant 10 is capable of being rapidly and easily stabilized in the stable, yet reversible, stretched configuration within a predetermined, practical temperature range in which it is easy to work and which does not require expensive equipment or procedures to maintain. For example, the predetermined temperature range may be formulated to extend from temperatures of −100° C. to 50° C. Preferably the temperature range will extend from about freezing, e.g., about 0° C., to temperatures at or near normal body temperature, e.g., at about 40° C. These exemplary predetermined stretch-crystallization stabilization temperatures may be achieved with simple refrigeration, liquid nitrogen, liquid $CO_2$, or simply by immersing implant 10 in an ice bath or in cool water.

Which stretch-crystallization temperatures are utilized will depend upon the physical properties of the stretch-crystallizable elastomers utilized in accordance with the teachings of the present invention. A number of exemplary novel silicone elastomers are disclosed herein with uniquely formulated stretch-crystallizable temperatures making them particularly suitable for forming medical implants that can be shape transformed at near ambient temperatures (20° C. to 25° C.) into the stable small-incision configurations of FIGS. 3, 4A and 4B. The stabilization of implant 10 in crystallized shape-transformed form may be accomplished within a few minutes or within a few seconds of being exposed to the appropriate predetermined temperatures. It should be noted that once stabilized, the elastomers remain substantially rigid and are less flexible, stretchable, or squeezable. Cooling the stretch-crystallized implant accelerates crystal formation within the stretched implant and stabilizes the transformed shape more rapidly. However, cooling is not essential to the practice of the present invention as the stabilizing crystals from over time as long as the implant is maintained in the deformed, shape-transformed configuration where stretch-crystallization occurs.

After being stabilized in the stretched shape-transformed, small-incision configuration, as exemplified in FIG. 3, implant 10 can be stored, transported, or manipulated by an implanting surgeon with a minimum of difficulty and without fear that it will revert to its non-stretch-crystallized configuration. This greatly facilitates its implantation as taught herein. Of equal importance, implant 10 is capable of rapidly recovering its original unstretched crystallized configuration and properties simply by allowing the implant to warm to body temperature following implantation. This occurs within seconds of implantation without additional action by the implanting surgeon. This substantially 100% recovery of the original configuration and properties includes recovery of the original size and shape in all three dimensions, and where appropriate includes index of refraction and optical clarity. In accordance with the present invention, the preferred melting-point temperature of implant 10 should range from about 25° C. (slightly above ambient) to normal body temperature or about 37° C.

Preferably, the elastomers from which exemplary implant 10 is made are stretchable to a stretch-crystallized configuration to a dimension that in at least one direction is at least about 300% to 600% greater than the original, unstretched dimension. For example, with exemplary implant 10 configured as an intraocular lens as shown in FIGS. 1 and 2, the lens may have an exemplary diameter D of about 9 mm and a central thickness T of about 4.5 mm when in the unstretched configuration. When in the stretched, rod- or blade-shaped, small-incision configuration, implant 10 may have a length l of about 40 mm to 50 mm and a diameter d of about 1 mm to 3 mm as shown in FIG. 4A. FIG. 4B shows an alternative blade-shaped cross-section which may mimic the shape of a surgical incision. This increase in one dimension from a 9-mm diameter D to a 50-mm length l represents nearly a 350% increase in this dimension. Concurrently with this 350% increase, lens implant 10 experiences a substantial decrease in at least one other dimension. In this example, from a 4.5-mm thickness T to a 1-mm diameter or cross-section d as shown in FIGS. 4A and 4B. This decrease represents about a 75% decrease in this dimension. More importantly, this decrease to a near 1-mm dimension means that implant 10 can be inserted into a patient through an incision which is relatively small when compared to that which would be required for implant 10 in the unstretched configuration. In this example, the implantation incision necessary to implant the stretched, rod-shaped configuration of FIG. 4 may be less than about 2 mm as opposed to the greater than 9-mm incision necessary for the implantation of the unstretched implant.

Those skilled in the art will appreciate that the volume of the implant remains relatively constant between the stretch-crystallized, shape-transformed configuration and the original, unstretched configuration. This places a practical constraint on the amount of stretching that can be imparted to the implant because reducing one dimension necessarily increases at least one other. As a result, if the diameter d of FIG. 4A is made too small, the length l of FIG. 3 becomes overly long. In the case of an intraocular lens implant 10 as illustrated in FIG. 1, stretching the lens too much will result in a rod-shaped implant configuration that is too long to fit into the intended implantation site within the eye. Thus, for a conventional 6-mm intraocular lens implant weighing approximately 20 mg, the implant can be stretch crystallized to a shape-transformed configuration approximately 20 mm long and 1 mm in diameter. Conversely, for a full-size intraocular lens implant weighing approximately 160 mg, the resultant stretch-crystallized shape-transformed implant will have a length of approximately 20 mm to 30 mm and a corresponding diameter of 2 mm to 3 mm. Stretching the full-sized intraocular lens to a 1-mm diameter would produce an implant nearly 160 mm long which could not be implanted into the eye. Naturally, for implants intended to be positioned in other locations within a patient's body, these constraints can be varied accordingly.

It should be noted at this point that one particularly unique advantage of the present invention is its functional impact on the exemplary intraocular lens implants disclosed herein. To date, full-size intraocular lenses have been difficult to implant due to the relatively large implantation incisions required. The associated implantation trauma may offset the intended advantages of the full-sized IOL which include eliminating decentration, tilt or misalignment of the lens following implantation. However, utilizing the teachings of the present invention a full-size IOL can now be implanted through a very small 3 mm to 4 mm implantation incision. This unique advantage of the present invention illustrates the relevance of the exemplary IOL embodiments as exemplary of the unprecedented features and advantages of the invention.

Figure 6:
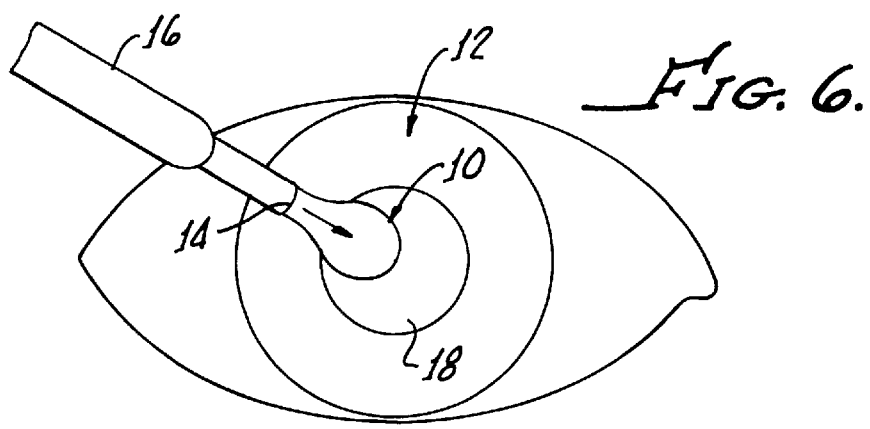
FIG. 6 is a view of the eye and exemplary stretch-crystallizable implant of FIG. 5, illustrating another step of the implantation procedure.
Figure 7:
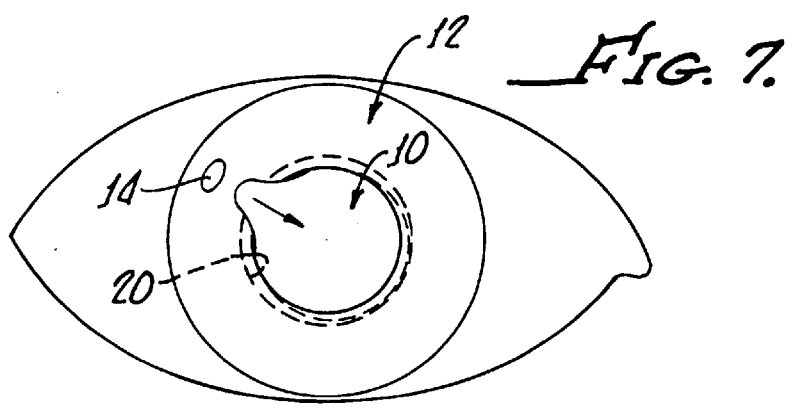
FIG. 7 is a view of the eye and exemplary stretch-crystallizable implant of FIG. 6, illustrating the implant in the unstretched configuration after implantation and recovery of its original configuration and physical properties.

With this re-emphasized understanding of the exemplary, non-limiting nature of the IOL implants disclosed herein, the associated broadly applicable methods of implantation provided in accordance with the teachings of the present invention will now be illustrated with reference to FIGS. 5–7. In a broad aspect, the implantation methodology of the present invention includes the simple steps of providing a stretch-crystallizable, shape-transformable implant, stretch crystallizing the implant into a stable, small-incision implant configuration, and inserting the stretch-crystallized implant through a small incision in a patient's body. This implantation method can include the additional step of cooling the stretch-crystallized implant to induce the formation of more stable, stronger, micro-crystals by accelerating the stretch-crystallization process. In either alternative, the stretch-crystallized small-incision implant configuration of the implant is sufficiently rigid and easily manipulable to allow the implanting surgeon to directly insert the shape-transformed implant through the small incision into an implantation target site within the patient's body.

Exemplary implant 10 may be stretched and/or squeezed into the stretched small-incision configuration by simple manipulation with medical implements, such as forceps, by pulling opposing portions of the implant away from each other. Preferably, implant 10 is formed of a material configured to allow this stretching and/or squeezing procedure to take place at near ambient or room temperatures. Once in the stretched configuration (e.g., as shown in FIG. 3), lens implant 10 may be stabilized in the small-incision implant configuration simply by holding implant 10 in the stretched position until stretch crystallization has proceeded to the point that the transformed shape will maintain itself. This process may take several seconds to several minutes depending on the materials, properties and volume. Because stretch crystallization actually raises the melting temperature of the crystals above that of the non-stretched implant material, the intended stretching conditions are below its new, higher melting point which will cool the implant into the stable, shape-transformed configuration. Preferably, in accordance with the teachings of the present invention, the small-incision implant configuration will be generally elongated with a circular, elliptical or blade-shaped cross-section as shown in FIGS. 3, 4A and 4B. As noted above, stabilization of the stretch-crystallized shape-transformed implant may be accelerated by immersion of the stretched implant into an ice or cool water bath which may have a temperature between 0° C. and about 4° C. in this exemplary embodiment. Implant 10 stabilizes in the crystalline stretched configuration within a short period of time, in this example, about 20 seconds.

Figure 5:
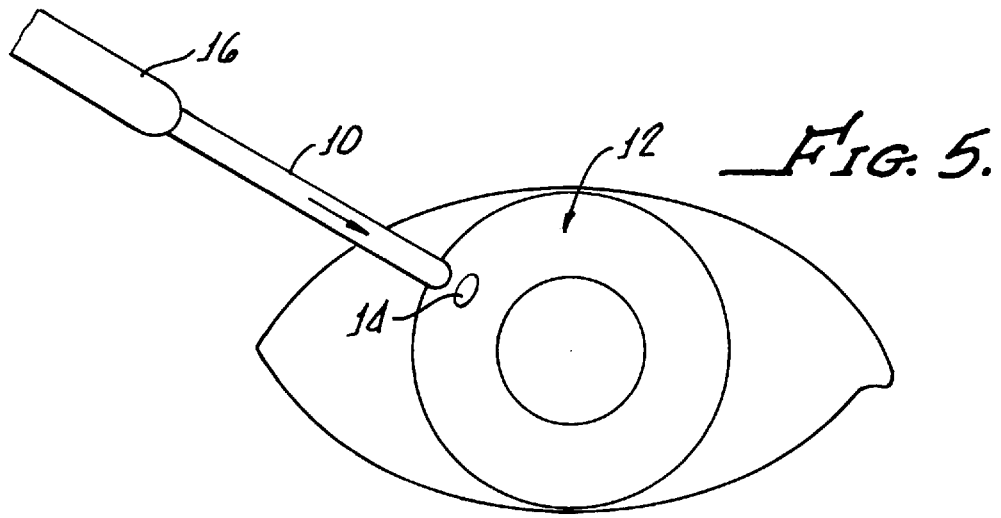
FIG. 5 is a view of an eye and an exemplary stretch-crystallizable implant in a stretched and stabilized configuration, particularly illustrating an implantation procedure in accordance with the present invention.

With specific reference to FIG. 5, implant 10 may be inserted though incision 14 by any suitable method. For example, forceps 16 holding one of the ends of the stretched implant may be used to push implant 10 through the incision. Forceps 16 may be cooled to a temperature below the melting point of implant 10 to prevent inadvertent warming of the implant. As mentioned above, implant 10 is substantially rigid when stabilized, which enables implant 10 to be easily manipulated during insertion. As shown in FIG. 6, when the stretch-crystallized implant 10 enters anterior chamber 18 of eye 12, implant 10 is subject to normal body temperatures within eye 12. Accordingly, implant 10 decrystallizes and begins to recover its original, unstretch-crystallized configuration. Within seconds of being fully inserted into eye 12, as shown in FIG. 7, implant 10 completely recovers to its original non-stretched configuration as it is positioned within a desired target site such as posterior chamber 20.

Figure 8:
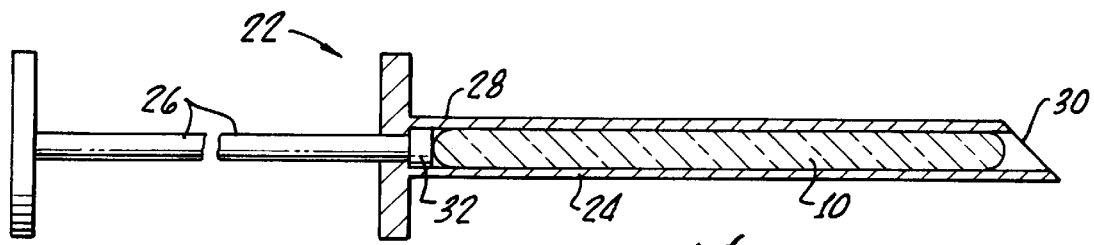
FIG. 8 is a cross-sectional view of an implantation device for implanting a stretch-crystallizable implant of the present invention.

Referring now to FIG. 8, an alternative implantation method embodiment is illustrated employing an implantation device 22 to place implant 10 in eye 12. Exemplary implantation device 22 includes a cannular portion 24 and a plunger 26. Plunger 26 includes an end piece 32 which is slidably received within chamber 28. Cannular portion 24 includes an inner chamber 28 and an outlet 30. Implant 10 is received within chamber 28 after being stretch crystallized into an elongated rod-or blade-shaped small-incision configuration.

Figure 9:
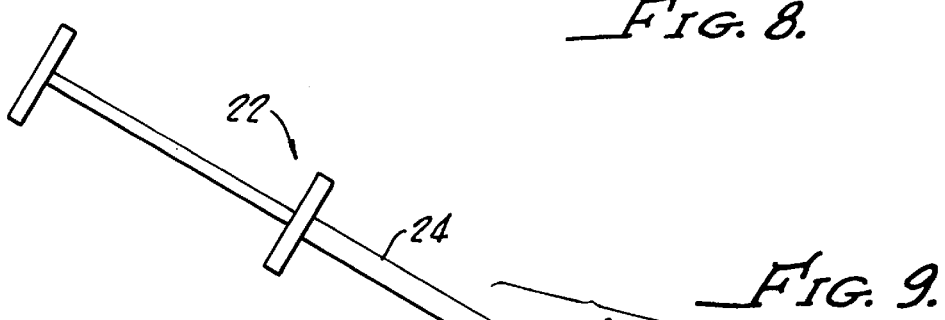
FIG. 9 is a diagrammatic fragmentary cross-sectional view of an eye and an exemplary implantation device, illustrating a primary step in an exemplary implantation procedure of the invention.

As shown in FIG. 9, rather than directly inserting stretch-crystallized small-incision implant 10 through an incision 14 in eye 12, outlet 30 of implantation device 22 may be directed into position within the patient's body to deposit implant 10 at the target site. Alternatively, the diameter of cannular portion 24 may be configured to be relatively small so as to function as a puncturing cannula analogous to a hypodermic needle. As such, cannular portion 24 is capable of forming its own incision or access pathway through tissue thereby eliminating the need to cut or form an incision with a separate step.

Cariular portion 24 may be cooled below the melting point of implant 10 so as to maintain the implant in the stabilized stretch-crystallized configuration. Cannular portion 24 may also function to insulate implant 10 from the relatively warm body temperature of the implantation site until the implant is pushed from implantation device 22. Maintaining implant 10 in the stabilized stretch-crystallized configuration prevents the implant from exerting any outward force on the walls of chamber 28 so that only a small force is required to push plunger 26 into cannular portion 24 to push implant 10 from outlet 30 into position at the implant target site. A viscoelastic fluid 28 such as Herlon® available from Pharmacia may be added to chamber 28 to provide lubrication.

Figure 10:
FIG. 10 is a diagrammatic fragmentary cross-sectional view of the eye and the exemplary implantation device, illustrating an implantation step subsequent to that shown in FIG. 9.
Figure 11:
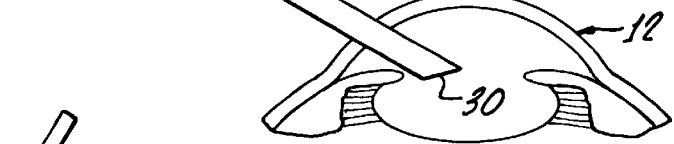
FIG. 11 is a diagrammatic fragmentary cross-sectional view of the eye and the exemplary implantation device, illustrating an implantation step subsequent to that shown in FIG. 10.

Regardless of whether outlet 30 is utilized to puncture its own access pathway or is simply inserted through a small surgical incision, once cannular portion 24 has been positioned within the patient's body with outlet 30 directed toward the implant target site, as shown in FIG. 10, plunger 26 is then pushed into cannular portion 24 to urge implant 10 into the target site. As illustrated in FIGS. 9–12A, the exemplary target site is the posterior chamber 20 of eye 12 and implant 10 is a full-sized intraocular lens implant.

Figure 12A:
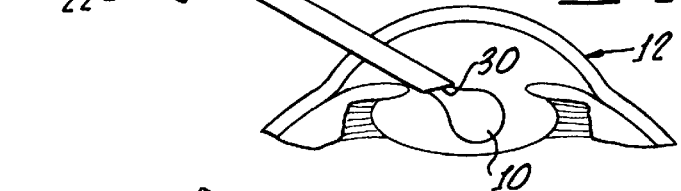
FIG. 12A is a diagrammatic fragmentary cross-sectional view of the eye and the exemplary implantation device, illustrating an implantation step subsequent to that shown in FIG. 11.
Figure 12B:
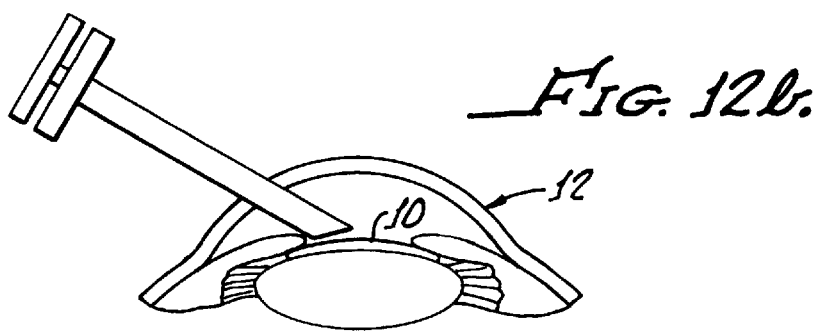
FIG. 12B is a diagrammatic fragmentary cross-sectional view of the eye and the exemplary implantation device, illustrating the implantation of an alternative implant.

Alternatively, where implant 10 is configured to function as an implantable contact lens intended to function in a position in front of the natural lens of the eye, implantation device 22 makes it possible to deliver the implant to the target site through a very small incision. This is because the 3 mm to 4 mm incision normally associated with cataract removal is unnecessary for the implantation of an implantable contact lens. Thus, nothing more than a simple puncture or minimal incision of sufficient size to accommodate the passage of implantation device 22 into the eye is necessary. As a result, implantation incisions on the order of 1 mm to 2 mm can be achieved with the present invention. Incisions this small may completely avoid the need for post implantation suturing and provide the implanting surgeon with practical access alternatives including scleral access directly into the posterior chamber 20 of eye 12 or corneal-scleral access to the anterior chamber 18 or posterior chamber 20 as shown in FIG. 12B. Again, it should be emphasized, that intraocular lens implants are illustrative of the principals of the present invention and are not intended to limit the invention to intraocular lenses alone.

Figure 13:
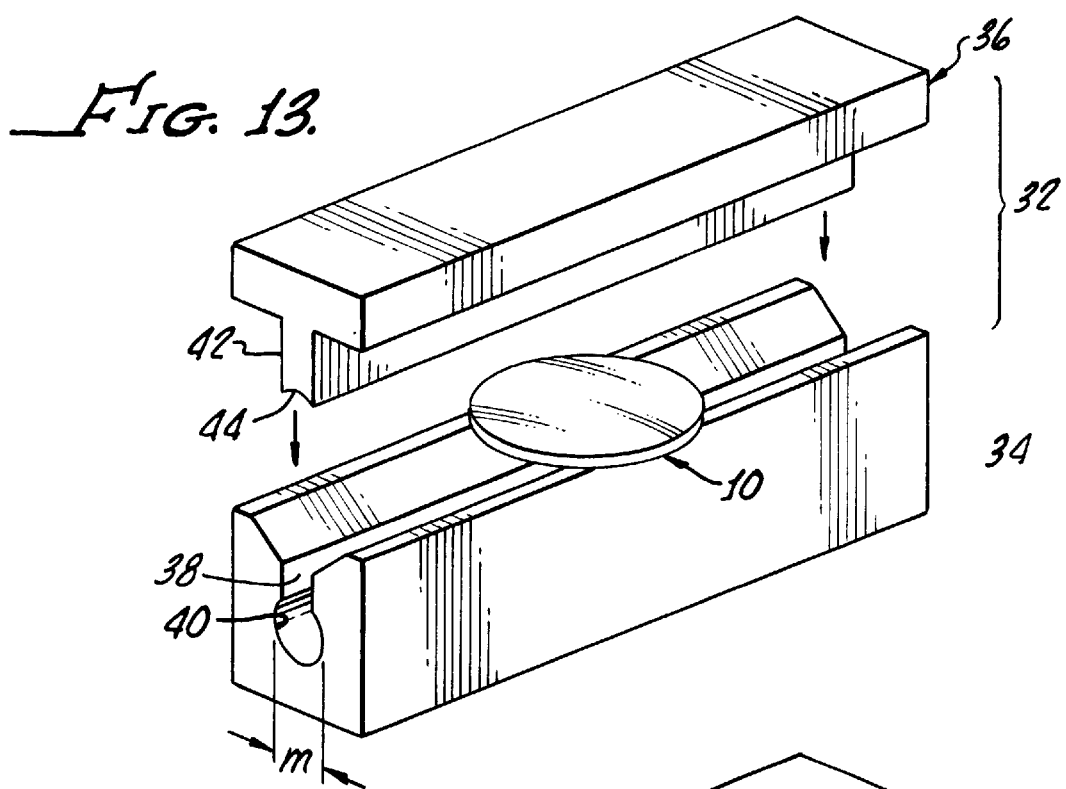
FIG. 13 is a perspective view of an assembly for shaping or configuring an exemplary stretch-crystallizable implant of the present invention into a stretch-crystallized configuration, illustrating the assembly prior to shaping the implant.
Figure 14:
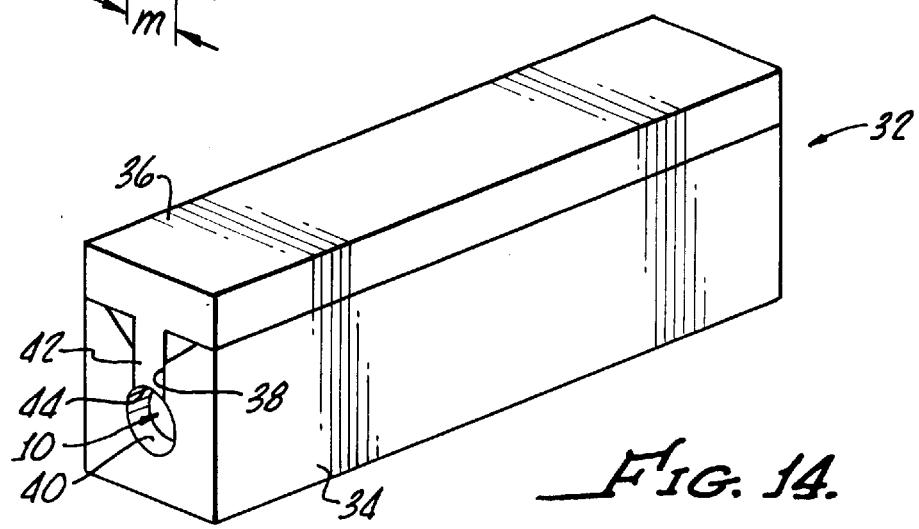
FIG. 14 is a view similar to that of FIG. 13, illustrating the assembly after shaping the implant into the stretch-crystallized configuration.

An alternative method for stretch crystallizing and shape transforming the implants of the present invention is illustrated FIGS. 13 and 14. Rather than simply pulling on opposing portions of implant 10 to stretch the implant in one direction, as shown in FIG. 13, implant 10 may be stretch crystallized into a deformed, stable, small-incision implant configuration with a compression jig generally indicated by reference 32. Compression jig 32 includes a female mold 34 and a compression plunger 36. Mold 34 is provided with a receiving slot 38 defining mold cavity 40. Compression plunger 36 is provided with a projecting guide 42 dimensioned to slidingly fit within receiving slot 38. Projecting guide 42 itself is provided with a mating face 44 which is dimensioned to engage with and complete the configuration of mold cavity 40 to define a small-incision implant configuration when projecting guide 40 is fully inserted into receiving slot 38. In use, a stretch-crystallizable implant, such as exemplary implant 10, is positioned within receiving slot 38 and projecting guide 42 of compression plunger 36 is pressed into receiving slot 38, driving implant 10 into mold cavity 40. This process compresses implant 10 into mold cavity 30 with a squeezing action causing implant 10 to stretch along the longitudinal axis defined by mold cavity 40. Water or a viscoelastic fluid may be used to facilitate the squeezing of implant 10 into mold cavity 40. Mold 34 and plunger 36 may include structure for guiding projecting guide 42 into receiving slot 38 in a consistent and controlled manner.

Those skilled in the art will appreciate that the stretching of implant 10 is not completely uniform throughout the extent of the implant material. Thus, different portions of implant 10 will be stretched to differing degrees. However, as shown in FIG. 10, when projecting guide 42 of compression plunger 36 has been completely received in receiving slot 38, implant 10 is significantly deformed into an elongate, blade- or rod-shaped small-incision implant configuration. Merely holding implant 10 in this configuration will result in the formation of stretch-crystallized transient stabilizing bonds within the material of implant 10 forming a stable shape-transformed stretch-crystallized implant. Alternatively, cooling stretch-crystallized implant 10 within compression jig 32 will accelerate and enhance this process. Cooling can be accomplished through the simple immersion of the compressed implant and compression jig assembly into a water bath or through simple refrigeration. In the exemplary embodiment of compression jig 32 shown in FIGS. 13 and 14, mold cavity 40 is configured to have a cross-sectional diameter or width m of 2.5 mm or less and a length ranging from 30 mm to 50 mm. This configuration is suitable for the stretch crystallization of full-size intraocular lens implants. Those skilled in the art will appreciate that alternative dimensions may be utilized as appropriate.

At this point it should be noted that although exemplary lens implant 10 shown in FIGS. 1 and 2 has a biconvex lens element, it is contemplated as being within the scope of the present invention to configure the light-focusing lens elements of the lens implants in any of a wide variety of optical lens configurations depending upon light-focusing needs or intended lens function and target site. Exemplary alternative cross-sectional lens shapes or configurations may include biconvex, plano-convex, plano-concave, or concavo-convex or meniscus, as known to those of ordinary skill in the art. Other alternative cross-sectional lens configurations are also within the scope of the present invention.

Further, although exemplary lens implant 10 is shown in FIG. 1 without any support structures or "haptics", it is contemplated as being within the scope of the present invention that lens implant 10 may include such support haptics, as is known to those of ordinary skill in the art. Such support haptics need not be made of the stretch-crystallizable elastomers and may include generally planar blade haptics, loop haptics, or even generally planar, circular flange support haptics. Other alternative haptic support configurations are also within the scope of the present invention, as dictated by the support and positioning needs of the individual patient or lens design.

Figure 15:
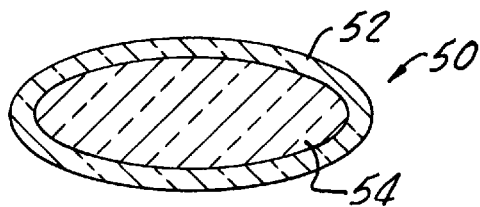
FIG. 15 is a cross-sectional view of another exemplary embodiment of a stretch-crystallizable implant configured as an intraocular lens in accordance with the present invention.

Lens implants made in accordance with the teachings of the present invention may also be formed as balloon-shaped lenses, such as implant 50 shown in FIG. 15. Balloon implant 50 has an elastomeric skin 52 which defines an inner chamber containing a more fluid material 54. Exemplary skin 52 may be on the order of about 0.2 mm thick, and material 54 typically has an index of refraction preferably ranging from about 1.38 to 1.46. Exemplary balloon implant 50 may be stretch crystallized by elongation or by compressive deformation in accordance with the procedure described in reference to FIGS. 13 and 14. Utilizing the teachings of the present invention, it is preferred that at least skin 52 be made of stretch-crystallizable elastomer. Alternatively, both skin 52 and inner elastomeric material 54 may be made of stretch-crystallizable elastomer although this is not essential to the practice of the present invention.

As those skilled in the art will appreciate, the unique functional advantages of the stretch-crystallizable elastomers of the present invention make it possible to manufacture and implant balloon lens 50 through a small incision in a pre-filled configuration. This eliminates the problems and complexities associated with attempting to inflate a balloon lens following implantation. More specifically, the balloon lens 50 of the present invention may be manufactured with controlled dimensions and optical properties prior to implantation. This is particularly advantageous for full-sized optics intended to complete fill the posterior chamber normally occupied by the natural lens. Because the stretch-crystallizable elastomeric skin 52 of balloon implant 50 can be significantly deformed without tearing or permanent deformation the balloon lenses of the present invention can be inserted through relatively small incisions with confidence that the optical performance of the lens will be appropriate for the particular patients involved.

Alternatively, it is also contemplated as being within the scope of the present invention to insert balloon lens 50 in an empty or deflated configuration. Then, a curable elastomer can be injected to inflate the implant to the desired final configuration. Because the curable inner material 54 is sealed within the biocompatible elastomeric skin 52, the risk of a complicating physiological reaction is avoided. As with the previously discussed pre-filled embodiment of balloon implant 50, the use of biocompatible skin 52 makes it possible to fine tune the physical properties of inner material 54 with reduced concern for biocompatibility. Thus, for optical purposes the refractive index of inner material 54 may be maximized without the biocompatibility concerns normally associated with direct contact between inner material 54 and body tissues or fluids. Alternatively, for non-optical implants intended for positioning in different target sites within a patient's body, different physical properties such as viscosity or density may be optimized with reduced concern for biocompatibility problems.

Once again, it should be emphasized that the scope and teachings of the present invention are not limited to the exemplary embodiments of intraocular lenses or lens implants. Accordingly, being cognizant of the broad scope of the present invention, the implants may be manufactured in accordance with the teachings thereof utilizing any suitable technique known in the art. For example, where appropriate, the implants may be cast, compression molded, injection molded, die cut or the like. The broad-based manufacturing capability of the present invention is particularly advantageous in connection with small implant structures such as the exemplary lens embodiments. Because the stretch-crystallizable materials of the present invention are suitable for casting and molding manufacturing techniques, the problems associated with precision matching of small implant structures can be avoided. As a result, significant portions of the implants may be formed of the elastomeric compounds with minimal complication. Other structural elements of the implants, such as lens haptics, may be cast in place using conventional manufacturing techniques.

Utilizing the teachings of the present invention, the stretch-crystallizable portion of the implants may be formulated to optimize stretch-crystallization and melting temperatures, optical clarity, refractive index, density, resiliency, volume, and post-stretching recovery as appropriate for the intended purpose of the implant. Because the elastomeric materials of the present invention do not require cross-linked fillers for strength, they resist permanent deformation when stretched. This allows the elastomeric materials to exhibit essentially 100% recovery of their original, non-stretched configurations, a particularly important feature for light focusing implants. By tuning the formulation of the stretch-crystallizable elastomeric materials, it is possible to fine tune the stretch-crystallization and melting recovery temperatures to those most appropriate for simplified implantation.

Because it is very common for contemporary physicians to store lens implants or other implants in refrigerated conditions prior to implantation, it may be preferable to configure the elastomeric implants of the present invention to stretch crystallize or freeze in the small-incision implant configuration at temperatures between 0° C. and 25° C. (normal room temperatures). Preferably, the melting temperature of the stretch-crystallized elastomers will be correspondingly tuned to a point near normal body temperature, approximately 37° C. Once the stretched crystallized elastomers begin to lose the structural or molecular order induced by stretching, the melting point will drop relative to the stretched crystallized melting point so that the implant is able to completely resume its non-stretch-crystallized configuration following implantation. Naturally, biocompatibility and the absence of free monomer that can leech from the elastomeric materials should be formulated into the implants to prevent subsequent complications.

Prior art stretch-crystallizable elastomeric materials typically possess melting points that are much lower than normal body temperature. As a result, they have not been practical for use as medical implants because they will not retain, easily manipulatable, stable, shape-transformed small-incision configurations. Moreover, where the intended implant use includes the function of light focusing, the known stretch-crystallizable materials have been impractical because they are hazy and lack an appropriate refractive index to function as a lens implant. Because the natural lens of the eye has a refractive index on the order of 1.4, it is preferred that stretch-crystallizable elastomeric materials utilized for lens implants in accordance with the teachings of the present invention have refractive indices on the order of 1.3 to 1.4 or greater. Higher refractive indicies will reduce the size, thickness, and volume of the lens necessary to obtain the desired optical result. More specifically, utilizing materials with a refractive index of 1.4 or greater enables the formation of optical lenses having diopters greater than 20. Lower refractive indices stretch-crystallizable materials can be utilized to form lenses having diopters on the order of 15 or less.

Regardless of whether or not the implant is intended to focus light, the stretch-crystallizable material should be formulated to fine tune the stretch-crystallized melting point to a temperature near or slightly below body temperature. An exemplary stretch-crystallizable elastomeric material that accomplishes this result can be formed in accordance with the teachings of the present invention from homopolymers or copolymers of what are know as $F_3$ monomers. Such polymerized exemplary silicone stretch-crystallizable elastomeric materials are exemplified by poly(methyl(3,3,3-triflouropropyl) siloxane). Preferably, these exemplary materials will have a cis/trans ratio ranging from 40/60 to 100/0. This will produce appropriate, tunable stretch-crystallizable melting temperatures. Utilizing the teachings of the present invention, it has been found that the cis form contributes to the stretch crystallization, and, therefore, higher melting-point materials can be formed if the cis/trans ratio is 40/60 to 100/0. Accordingly, relatively higher stretch-crystallized melting point materials can be formed by raising the cis/trans ratio to ratios on the order of 60/40.

Where the intended use of the stretch-crystallizable elastomeric material is the formation of a light focusing implant, it may be necessary to copolymerize the polymerized $F_3$ monomer with a compatible monomer having a higher refractive index. For example, compounds known in the art as $D_3$ monomers typically have higher refractive indices than $F_3$ monomers. Diphenyl $D_3$, also known as hexaphenylcyclotrisiloxane is such a high refractive index monomer. Forming a copolymer of from 60% to 100% of an $F_3$ monomer and between 0% and 40% of the $D_3$ monomer provides those skilled in the art with the capability of fine tuning the refractive index of the resultant copolymer. The more $D_3$ monomer incorporated into the copolymer, the higher the refractive index. As those skilled in the art will appreciate, it may be difficult to incorporate more than 40% of the $D_3$ monomer into the intended copolymer material.

A further understanding of the present invention will be accorded to those skilled in the art from a consideration of the following, non-limiting examples. These examples illustrate the formulation and fine tuning chemical manipulation of the physical properties of exemplary stretch-crystallizable elastomeric materials. Before proceeding, it should be emphasized that these examples are illustrative of the principles of the present invention and are not intended to limit the scope of the invention to the exemplary elastomeric materials alone.

EXAMPLE 1

As a preliminary step in the formation of exemplary stretch-crystallizable elastomers in accordance with the teachings of the present invention, a difunctional initiator is prepared for use in the formation of subsequent homopolymers and copolymers. For purposes of illustration, exemplary stretch-crystallizable materials are silicone elastomers. Accordingly, two (2) grams of diphenyl silanediol were dried at 110° C. under vacuum for 30 minutes. After cooling to room temperature and purging with argon (Ar) gas, 7.5 milliliters (ml) of toluene and 7.5 ml of THF were added to obtain a clear solution. Ten (10) microliters ($\mu$l) of styrene were then added as an indicator. Approximately 8 ml of butyl lithium (with a concentration of about 2.5 M in hexane) were added drop-wise until the solution just turned slightly yellow to form a solution of difunctional initiator for use in forming the exemplary stretch-crystallizable elastomers.

EXAMPLE 2

To form an exemplary stretch-crystallizable elastomeric homopolymer, ten (10) grams (about 8 ml) of $F_3$ monomer, i.e., methyl(3,3,3-triflouropropyl)siloxane, with a cis content of about 60% and trans content of about 40%, were added to a 125 ml reaction flask, dried at 80° C. under vacuum for 30 minutes, and then cooled to room temperature. The cis/trans ratio of 60/40 was chosen to fine tune the melting-point temperature of the material, following stretch crystallization, to near normal body temperature. Lower cis/trans ratios produce a material whose melting point would be lower than normal body temperature.

One (1) ml of THF and 7 ml of methylene chloride ($CH_2Cl_2$) were then added and stirred for a few minutes. One (1) ml of the difunctional initiator of Example 1 was added to initiate reaction at room temperature under Argon (Ar) gas. After 4 hours the reaction was terminated by adding 0.5 ml of vinyldimethylchlorosilane and triethylamine. After washing with distilled water, dissolving the THF, and precipitating with methanol, more than 8 grams of $F_3$ polymer were collected. The hompolymer was glass clear with a number average molecular weight, $M_n$, of 40,000, a polydispersity of 1.1, and a refractive index of 1.383.

The $F_3$ homopolymer can be crosslinked by mixing 5 grams of the $F_3$ homopolymer with 2 $\mu$l of platinum (Pt) catalyst (with a Pt concentration of 2.5%), 8 $\mu$l of inhibitor, and 45 $\mu$l of tetrekis(dimethylsiloxy)silane crosslinker and degassing the viscous liquid by centrifuging.

This produced a crosslinked poly(methyl(3,3,3-triflouropropyl)-siloxane) $F_3$ copolymer with a cis/trans ratio of approximately 60/40, and a refractive index of 1.383. The silicone elastomer was optically clear with excellent mechanical strength and exhibited a superior elongation in one direction of more than 600%. The polymer was easily stretch crystallized into a stable transformed shape at temperatures below 20° C. Warming the stretch-crystallized material to a temperature of approximately 35° C. resulted in the material recovering its original shape within a few seconds. This material was utilized to form plate style intraocular lenses with a 6-mm optical zone. Stretching these lenses into a long, thin rod approximately 40 mm in length and cooling the stretched lenses in a cold water bath at approximately 0° C. to 4° C. produced a stable, relatively rigid rod shaped implant that was easily manipulated by hand or with forceps. Warming the shape-frozen rod to a temperature between 30° C. to 40° C. resulted in the rod returning to its original plate intraocular lens configuration in under five seconds. The optical resolution of the lens remained unchanged by this process. Because of the relatively low refractive index, a practical intraocular lens with a 6-mm optical zone utilizing this exemplary material would have an upper diopter limit of approximately 15.

Because the majority of intraocular lens users require lenses having diopters on the order of 20 or greater, a higher refractive index stretch-crystallizable elastomeric material was prepared by copolymerizing the homopolymer of Example 2 with a higher refractive index monomer as discussed in the following example.

EXAMPLE 3

In order to produce an exemplary stretch-crystallizable elastomer having a higher refractive index than the homopolymer of Example 2, eight (8) grams of the $F_3$ monomer of Example 2 (with cis content about 60% and trans content about 40%) and 2 grams of diphenyl $D_3$, or hexaphenylcyclotrisiloxane, were added to a 125-ml reaction flask, dried at 110° C. under vacuum for 30 minutes, and cooled to 45° C. (oil bath temperature). Two (2) ml of THF and 14 ml of methylene chloride ($CH_2CL_2$) were added to the cooled solution and stirred for a few minutes until the diphenyl $D_3$ was completely dissolved. 0.5 ml of the difunctional initiator of Example 1 was added to the reaction flask and the mixture refluxed at 45° C. under argon gas. After 10 hours, the reaction was terminated by cooling to room temperature and then adding 0.2 ml of vinyldimethylchlorosilane and triethylamine. After washing with distilled water and toluene and being precipitated by hexane, 6 grams of copolymer were obtained. The copolymer was glass clear with a $M_n$ of 50,000 and a refractive index of 1.408. If desired, the copolymer can be crosslinked by mixing five (5)

grams of the copolymer with 2 μl of a platinum catalyst (with a Pt concentration of 2.5%), 8 μl of inhibitor, and 40 μl of tetrekis(dimethylsiloxy)silane crosslinker and degassing the mixture by centrifuging.

As with Example 2, an elastomeric strip was produced by curing the copolymer of Example 3 at a temperature between 100° C. to 140° C. for several minutes. This produced an optically transparent, glass clear stretch-crystallizable elastomer exhibiting excellent mechanical strength and superior elongation of more than 600% in one direction. The elastomeric material exhibited stable, stretch crystallization and shape transformation at temperatures below 4° C. Warming the stretch-crystallized elastomer to 35° C. resulted in the material recovering its original shape within a few seconds.

The optical clarity and high refractive index of this exemplary stretch-crystallizable elastomeric copolymer facilitated the production of exemplary intraocular lenses having dipoters ranging between 20 to 25. Six plate style intraocular lenses were molded from the exemplary copolymer elastomer of Example 3 by molding at 140° C. for five minutes. The optical resolutions of these experimental lenses were measured using conventional techniques and found to be comparable to commercially available intraocular lenses made with conventional, non-stretch-crystallizable materials. In contrast to the prior art lenses, the exemplary stretch-crystallizable lenses were capable of being stretched to at least 5 times their original length and, following cooling in an ice water bath, remained stably shaped transformed in their stretch-crystallized elongated shapes. Dipping the stretch-crystallized lenses in warm water at approximately 35° C. resulted in the lenses immediately recovering their original shapes. Following shape recovery, the optical resolution of the lenses was again measured and compared with their pre-stretch-crystallization values. The post-stretching and recovery resolutions were the same or better than before the lenses were stretch crystallized. Additionally, a difference of less than 0.2% was measured between the dimensions of the pre-stretched crystallized and post-stretched crystallized lenses.

To demonstrate the ability to fine tune the physical properties of the exemplary tretch-crystallizable elastomers through modified formulation techniques, a variation of the opolymer formation protocol of Example 3 was conducted.

EXAMPLE 4

The reaction of Example 3 above was carried out with a reaction time of 21 hours rather than the original 10 hours. As before, the reaction was terminated by cooling to room temperature and then adding 0.2 ml of vinyldimethylchlorosilane and triethylamine. After washing with distilled water and toluene and precipitation by hexane, 7 grams of copolymer were collected. The copolymer was optically clear with a molecular weight ($M_n$) of 53,000 and a refractive index of 1.418.

This higher refractive index makes it possible to utilize this particular formulation of the exemplary stretch-crystallizable copolymer in intraocular lenses having thinner cross sections and smaller volumes. However, this benefit may be offset by an associated decrease in the mechanical strength and elongation of this exemplary material. Upon cross linking this exemplary elastomeric material utilizing the procedure detailed in Example 3, the polymer exhibited an elongation less than 200%. As a result, the benefit achieved with the higher index may be offset by the inability to stretch crystallize the material to the extent achieved with the copolymer of Example 3. Nonetheless, the material may be suitable for stretch-crystallizable implants other than intraocular lenses.

Further efforts at fine tuning or adjusting the properties of the exemplary stretch-crystallizable elastomers of the present invention were conducted by modifying the reaction temperature as follows.

EXAMPLE 5

The reaction of Example 3 was repeated only the temperature of the oil bath was raised from 45° C. to 70° C. After 10 hours of reaction time, the reaction was terminated by cooling to room temperature and adding 0.2 ml of vinyldimethylchlorosilane and triethylamine. After washing with distilled water and toluene and precipitating by hexane, 7 grams of copolymer were obtained. The copolymer was glass clear with a molecular weight ($M_n$) of 54,000 and a refractive index of 1.40. Crosslinking the copolymer as before yielded an elastomer with mechanical strength similar to that of Example 3. Accordingly, this exemplary elastomeric stretch-crystallizable copolymer material exhibited physical and mechanical properties that are suitable for use as medical implants including intraocular lenses.

Additional modifications of the exemplary formulation protocols are provided by the following non-limiting examples which provide further illustration of the ability to modify and fine tune the physical and mechanical properties of the exemplary elastomeric materials of the present invention.

EXAMPLE 6

The reaction of Example 3 was carried out as before with the reaction temperature decreased from 45° C. to room temperature and the reaction time increased from 10 hours to 21 hours. After 21 hours of reaction time, a small amount of the material was removed from the reaction, and the refractive index was measured to be 1.390. The reaction was terminated after 48 hours by cooling to room temperature and adding 0.2 ml of vinyldimethylchlorosilane and triethylamine. After washing with distilled water and toluene and precipitating by hexane, 7 grams of copolymer were obtained. The copolymer was glass clear with a molecular weight ($M_n$) of 36,000 and a refractive index of 1.392. Crosslinking this material produced a stretch-crystallizable elastomer that exhibited weaker mechanical strength than that of Example 3. This reduction in refractive index and mechanical strength may make this material unsuitable for use as intraocular lens implants. However, it may be appropriate for other implant purposes.

EXAMPLE 7

The reaction of Example 4 above was carried out as before, except that the solvent was changed from methylene chloride to THF. A total of 16 ml THF was used in place of the THF methylene chloride solvent of Example 3. After 2 hours of reaction, the solution became less viscous. The reaction was terminated by cooling to room temperature and then adding 0.2 ml of vinyldimethylchlorosilane and triethylamine. After washing with distilled water and toluene and precipitating by methanol, substantially no polymer was obtained.

EXAMPLE 8

The reaction of Example 9 above was carried out as before with the temperature of the reaction reduced to room temperature. After 2 hours of reaction, the solution became less viscous. The reaction was terminated by cooling to room temperature and then adding 0.2 ml of vinyldimethylchlorosilane and triethylaamine. After washing with distilled water and toluene and precipitating by methanol essentially no polymer was obtained.

EXAMPLE 9

An alternative stretch-crystallizable elastomeric silicone copolymer was formed utilizing the protocol of Example 3 with an alternative comonomer by substituting phenylmethyl $D_3$, or 1,3,5-phenyl-2,4,6-methylcyclosiloxane for diphenyl $D_3$. As before, eight (8) grams of the $F_3$ monomer of Example 3 (with a cis content about 60% and a trans content about 40%) and 2 grams of phenylmethyl $D_3$ were added to a 125 ml reaction flask, dried at 80° C. under vacuum for 30 minutes and cooled to 45° C. (oil bath temperature). Two (2) ml of THF and 8 ml of methylene chloride ($CH_2CL_2$) were added, and the solution was stirred for a few minutes. 0.5 of the difunctional initiator was added to the reaction flask and the mixture was refluxed at 45° C. under argon (Ar) gas. After 10 hours of reaction, the solution became viscous and the reaction was terminated by cooling to room temperature and adding 0.2 ml of vinyldimethylchlorosilane and triethylamine. After washing with distilled water and toluene and precipitating with methanol, a polymer was obtained with a refractive index of 1.383 indicating that no copolymerization took place.

EXAMPLE 10

The reaction of Example 9 was carried out as before with the temperature of the reaction increased to 110° C. (oil bath temperature). After 5 hours of reaction, the solution became viscous and the reaction was terminated by cooling to room temperature and adding 0.2 ml of vinyldimethylchlorosilane and triethylamine. After washing with distilled water and toluene and precipitating with methanol, a polymer was obtained with a refractive index of 1.383, indicating that no copolymerization took place.

Those skilled in the art will understand that the preceding exemplary embodiments of the present invention provide the foundation for numerous alternatives and modifications thereto. These other modifications are also within the scope of the present invention. Thus, by way of example, but not of limitation, the stretch-crystallizable implants of the present invention may be configured to function as cosmetic implants for reconstructive or augmentation purposes. Such implants would include artificial chins, cheekbones, noses, ears and other body parts including breasts and penile implants. Similarly, alternative implantation devices may be used to function with such implants in accordance with the principles and teachings of the present invention. In this manner, a wide variety of implants may be surgically inserted and positioned through minimal, relatively atraumatic surgical incisions. Accordingly, the present invention is not limited to that precisely as shown and described in the present invention.

We claim:

1. An improved medical implant formed of a stretch-crystallizable, shape-transformable elastomer.

2. The medical implant of claim 1 further comprising an additional element formed of a non-stretch-crystallizable material.

3. The medical implant of claim 1 wherein said elastomer is a stretch-crystallizable silicone.

4. The medical implant of claim 3 wherein said stretch-crystallizable silicone is selected from the group consisting of homopolymers of methyl(3,3,3-triflouropropyl)siloxane and copolymers of methyl(3,3,3-triflouropropyl)siloxane and hexaphenylcyclotrisiloxane.

5. The medical implant of claim 4 wherein said methyl (3,3,3-triflouropropyl)siloxane has a cis/trans ratio ranging from about 40/60 to 100/0.

6. The medical implant of claim 5 wherein said stretch-crystallizable silicone has a crystallization temperature ranging from –100° C. to 50° C.

7. The medical implant of claim 5 wherein said stretch-crystallizable silicon has a crystallization temperature ranging from –20° C. to 50° C. and a recovery temperature ranging from 0° C. to 50° C.

8. The medical implant of claim 5 wherein said stretch-crystallizable silicone is optically transparent and has a refractive index ranging from 1.38 to 1.46.

9. The medical implant of claim 5 wherein said stretch-crystallizable silicone stretch crystallizes at elongations of about 300% to 600%.

10. The medical implant of claim 9 configured to function as an intraocular lens.

11. An intraocular implant configured for reduced trauma implantation and having a light focusing optical portion formed of a stretch-crystallizable, shape-transformable silicone elastomer having a refractive index ranging from about 1.38 to 1.46.

12. The intraocular implant of claim 11 wherein said implant is an intraocular lens.

13. The intraocular implant of claim 12 wherein said intraocular lens includes a balloon lens.

14. The intraocular implant of claim 12 further comprising a haptic.

15. The intraocular implant of claim 11 wherein said implant is an implantable contact lens.

16. The intraocular implant of claim 11 wherein said stretch-crystallizable silicone is selected from the group consisting of homopolymers of methyl(3,3,3-triflouropropyl)siloxane and copolymers of methyl(3,3,3-triflouropropyl)siloxane and hexaphenylcyclotrisiloxane.

17. The intraocular implant of claim 16 wherein said methyl(3,3,3-triflouropropyl)siloxane has a cis/trans ratio ranging from about 40/60 to 100/0.

18. The intraocular implant of claim 16 wherein said stretch-crystallizable silicone has a crystallization temperature ranging from –100° C. to 50° C.

19. The intraocular implant of claim 16 wherein said stretch-crystallizable silicon has a crystallization temperature ranging from –20° C. to 50° C. and a recovery temperature ranging from 0° C. to 50° C.

20. The intraocular implant of claim 16 wherein said stretch-crystallizable silicone stretch crystallizes at elongations of about 300% to 600%.

21. A reduced trauma surgical implantation method comprising the steps of:

providing a stretch-crystallizable, shape-transformable implant;

stretch crystallizing said implant into a stable, small-incision implant configuration; and inserting said stretch-crystallized implant through a small incision into a patient's body.

22. The surgical implantation method of claim 21 further comprising the additional step of cooling said implant following said stretch-crystallization step.

23. The surgical implantation method of claim 21 wherein said stable small-incision implant configuration is an elongated rod or blade.

24. The surgical implantation method of claim 23 further comprising the additional step of loading said stretch-crystallized small-incision configuration implant into an implantation device having an outlet end prior to said inserting step.

* * * * *